(12) United States Patent
Hines et al.

(10) Patent No.: US 7,268,662 B2
(45) Date of Patent: Sep. 11, 2007

(54) PASSIVE SAW-BASED HYDROGEN SENSOR AND SYSTEM

(75) Inventors: Jacqueline H. Hines, Annapolis, MD (US); Leland P. Solie, Chetek, WI (US)

(73) Assignee: Applied Sensor Research & Development Corporation, Arnold, MD (US)

( * ) Notice: Subject to any disclaimer, the term of this patent is extended or adjusted under 35 U.S.C. 154(b) by 0 days.

(21) Appl. No.: 11/335,044

(22) Filed: Jan. 19, 2006

(65) Prior Publication Data

US 2007/0052516 A1 Mar. 8, 2007

Related U.S. Application Data

(60) Provisional application No. 60/714,559, filed on Sep. 7, 2005.

(51) Int. Cl.
*H01C 7/00* (2006.01)
(52) U.S. Cl. ............... 338/34; 338/28; 73/23.2; 73/24.01; 528/25
(58) Field of Classification Search ........ 338/13, 338/25, 27, 28, 34, 35; 73/23.2, 24.01, 24.06, 73/31.05; 528/25, 29; 436/149
See application file for complete search history.

(56) References Cited

U.S. PATENT DOCUMENTS

| | | | |
|---|---|---|---|
| 6,029,500 A * | 2/2000 | Tom | 73/31.05 |
| 6,114,943 A | 9/2000 | Lauf | |
| 6,630,560 B2 * | 10/2003 | McGill et al. | 528/25 |
| 7,047,792 B1 * | 5/2006 | Bhethanabotla et al. | 73/24.01 |
| 2004/0029288 A1 * | 2/2004 | Snow et al. | 436/149 |
| 2006/0112756 A1 * | 6/2006 | Xu et al. | 73/23.2 |

OTHER PUBLICATIONS

Barr, A.; "The Effect of Hydrogen Absorption on the Electrical Conduction in Discontinuous Palladium Films"; Thin Solids; 1977; pp. 217-226; 41; Elsevier Sequoia S.A.; Lausanne, NE.

Domansky, K. et al.; "Development and Calibration of Field-Effect Transistor-Based Sensor Array for Measurement of Hydrogen and Ammonia Gas Mixtures in Humid Air"; Analytical Chemistry; Feb. 1, 1998; pp. 473-481; vol. 70, No. 3; American Chemical Society; Richland, Wash.

(Continued)

*Primary Examiner*—Richard K. Lee
(74) *Attorney, Agent, or Firm*—Schiff Hardin LLP

(57) ABSTRACT

A hydrogen detecting system is characterized by a passive surface acoustic wave (SAW) sensor. The sensor includes a piezoelectric substrate having a self assembled monolayer arranged on at least a portion of the substrate to create a hydrophobic surface. A palladium nanocluster thin film is deposited on the monolayer and an interdigital SAW transducer is disposed upon the piezoelectric substrate for conversion of an RF signal into an acoustic wave and vice versa. At least one additional SAW element is also disposed on the substrate and spaced from the SAW transducer. The SAW element receives a signal from the SAW transducer and produces a response signal. The response signal is modified by the palladium nanocluster film due to a change in conductivity of the palladium nanocluster film upon exposure to hydrogen. This change in the response signal is measured by an interrogator, and yields a measure of the hydrogen concentration to which the sensor was exposed.

18 Claims, 13 Drawing Sheets

OTHER PUBLICATIONS

Dankert, O. and Pundt, A.; "Hydrogen-Induced Percolation in Discontinuous films"; Applied Physics Letters; Aug. 26, 2002; pp. 1618-1620; vol. 81, No. 9; American Institute of Physics; Melville, New York.

Du, X. et al.; "A New Highly Selective $H_2$ Sensor Based on $TiO_2$/PtO-Pt Dual-layer Films"; Chemical Materials; 2002; pp. 3953-3957; vol. 14, No. 9; American Chemical Society; Richland, Wash.

Yun, M. et al; "Electrochemically Grown Wires for Individually Addressable Sensor Arrays"; Nano Letters; 2004; pp. 419-422; vol. 4, No. 3; American Chemical Society; Richland, Wash.

Kwok, W. et al.; "Palladium Based Hydrogen NanoSensors"; Argonne National Laboratory; 2005; http://chemistry.anl.gov/MSDReview/SoftMaterials/Palladiumnanosensors.pdf.

Ltuz, B. et al.; "Hydrogen Sensing by Enzyme-Catalyzed Electrochemical Detection"; Analytical Chemistry; Aug. 1, 2005; pp. 4969-4975; vol. 77, No. 15; American Chemical Society; Richland, Wash.

Xu, T. et al.; "Self-Assembled Monolayer-Enhanced Hydrogen Sensing with Ultrathin Palladium Films"; Applied Physics Letters; 2005; pp. 203104-1-203104-3; vol. 86; American Institute of Physics; Melville, New York.

Ceramic Processing Group; "Thick-Film Hydrogen Sensor"; Oak Ridge National Laboratory; Aug. 22, 2005; http://ms.ornl.gov/researchgroups/process/cpg/sensor.html.

Fuel Cell Works; "New Hydrogen Sensor Faster, More Sensitive"; Argonne National Laboratory; Aug. 22, 2005; http://www.fuelcellswork.com/Suppage2722.html.

Hunter, G.; "Hydrogen Sensors Demonstrated on the Shuttle"; NASA Glenn Research Center; Aug. 22, 2005, http://lerc.nasa.gov/WWW/RT1999/5000/5510hunter.html.

Messer, A.; "Titania Nanotubes Make Supersensitive Hydrogen Sensors"; EurekAlert; Aug. 22, 2005; http://eurekaler.org/pub_releases/2003-07/ps-tnm072903.php.

Unknown; "Hydrogen Specific Sensing Systems"; $H_2$ Scan; Aug. 28, 2005; http://h2scan.com.

Unknown; "Robust Hydrogen Sensor"; $H_2$ Scan; Aug. 28, 2005; http://h2scan.com/technology.html.

Hunter, G.; "Automated Hydrogen Gas Leak Detection System"; NASA Glenn Research Center; Aug. 28, 2005; http://grc.nasa.gov/WWW/RT1995/2000/2510.html.

Hunter, G.; "Chemical Species Gas Sensors"; NASA Glenn Research Center; Aug. 28, 2005; http://grx.nasa.gov/WWW/chemsensors.

McDaniel, A.; "Chemical Sensors"; Sandia National Laboratories; Aug. 28, 2005; http://ca.saniea.gov/hydrogen/research/safetyCodesStandards/chemicalsensors.htm.

Jakubik, W., Urbanczyk, Kochowski and Bodzenta. "Bilayer Structure for Hydrogen Detection in a Surface Acoustic Wave Sensor System" Sensors & Actuators B 82 (2002), p. 265-271.

Jakubik, W., Urbanczyk and Opilski. "Sensor Properties of Lead Phthalocyanine in a Surface Acoustic Wave System" Ultrasonics 39 (2001), p. 227-232.

Jakubik, W. "Hydrogen Detection by Single and Bilayer Sensor Structures in Surface Acoustic Wave System" Journal of Physics IV France 129 (2005), p. 117-120.

Jakubik, W. "Hydrogen sensor with palladium and metal-free phthalocyanine bilayer structures in surface acoustic wave and electric systems" Molecular and Quantum Acoustics 24 (2003), p. 81-87.

Jakubik, W., Urbanczyk, Kochowski, Bodzenta. "Palladium and Phthalocyanine Bilayer Films for Hydrogen Detection in a Surface Acoustic Wave Sensor System" Sensors and Actuators B 96 (2003), p. 321-328.

Jakubik, W., Urbanczyk and Maciak. "Palladium and Metal-Free Phthalocyanine Bilayer Structures for Hydrogen Detection in the SAW Sensor System Based on Interaction Speed" IEEE Sensors Journal 6.5 (2006), p. 1178-1185.

Bekaroglu, O. "Synthesis of Phthalocyanines and Related Compounds" Journal of Porphyrins and Phthalocyanines 4 (2000), p. 465-473.

Palmgren, P., Priya, Niraj, Gothelid. "Self-Ordering of Metal-Free Phthalocyanine on InAs(100) and InSb(100)" Journal of Physics: Condensed Matter 18 (2006), p. 10707-10723.

Alfredsson, Y. et al. "Phase and molecular orientation in metal-free phthalocyanine films on conducting glass" Thin Solid Films 493 (2005) 13-19.

Narayanan Unni, K., and Menon. "Electrical and Optical Studies on Metal-Free Phthalocyanine Thin Films" Journal of Materials Science Letters 20 (2001), p. 1207-1209 Cook, M. "Phthalocyanine Thin Films" Pure Applied Chemistry 71.11 (1999), p. 2145-2151.

Morris, J., and Wu. "Modelling Conduction in Asymmetrical Discontinuous Metal Thin Films" Thin Solid Films 317 (1998), p. 178-182.

Kalli, K., Othonos, and Christofides. "Characterization of Reflectivity Inversion, $\alpha$- and $\beta$-Phase Transitions and Nanostructure Formation in Hydrogen Activated Thin Pd Films on Silicon Based Substrates" Journal of Applied Physics 91.6 (2002), p. 3829-3840.

Morris, J., Kiesow, Hong, and Wu. "Effects of Hydrogen Absorption on the Electrical Conduction of Discontinuous Palladium Thin Films" International Journal of Electronics 81.4 (1996), p. 441-447.

Othonos, A., Kalli, and Tsai. "Optically Thin Palladium Films on Silicon-Based Substrates and Nanostructure Formation: Effects of Hydrogen" Applied Surface Science 161 (2000), p. 54-60.

Baykara, N., Andzelm, and Salahub. "Hydrogen Chemisorption on, and Diffusion Through, Palladium Clusters" International Journal of Quantum Chemistry 29 (1986), p. 1025-1032.

Lewis, F. "Solubility of Hydrogen in Metals" Pure & Applied Chemistry 62.11 (1990), p. 2091-2096.

Suleiman, M., Jisrawi, Dankert, Reetz, Bahtz, Kirchheim, and Pundt. "Phase Transition and Lattice Expansion During Hydrogen Loading of Nanometer Sized Palladium Clusters" Journal of Alloys and Compounds 356-357 (2002), p. 644-648.

D'Amico, A. and Verona, E. "Hydrogen Sensor Using a Palladium Coated Surface Acoustic Wave Delay-Line" IEEE Ultrasonics Symposium (1982), p. 308-311.

Vetelino, J., Lade, and Falconer. "Hydrogen Sulfide Surface Acoustic Wave Gas Dectector" IEEE Transactions on Ultrasonics, Ferroelectrics, and Frequency Control UFFC-34.2 (1987), p. 156-161.

Nieuwenhuizen, M. and Barendsz. "Processes Involved at the Chemical Interface of a SAW Chemosensor" Sensors and Acuators 11 (1987) p. 45-62.

Lec, R., Vetelino, Falconer, and Xu. "Macroscopic Theory of Surface Acoustic Wave Gas Microsensors" IEEE Ultrasonics Symposium (1988), p. 585-589.

Xu, T. et al; "Self-Assembled Monolayer-Enhanced Hydrogen Sensing with Ultrathin Palladium Films"; Applied Physics Letters; 2005; p. 203104-1-203104-2; vol. 86; American Institute of Physics; Melville, NY.

Xu, T., Zach, Xiao, Rosenmann, Welp, Kwok, and Crabtree. "Self-assembled monolayer-enhanced hydrogen sensing with ultrathin palladium films" Applied Physics Letters 86 (2005), p. 203104.1-203104.3.

* cited by examiner

PASSIVE SAW-BASED HYDROGEN SENSOR AND SYSTEM

This application claims the benefit U.S. provisional application No. 60/714,559 filed on Sep. 7, 2005.

BACKGROUND OF THE INVENTION

The search for alternative energy sources is driven by the desire to be independent from foreign sources of fossil fuels, to reduce the pollution caused by use of fossil fuel, and to reduce production of green house gases that can add to global warming. Hydrogen is a fuel that satisfies all of these needs as it can be produced from abundantly available materials such as water, it produces no pollutants and no greenhouse gases as byproducts, and it can be converted to heat through combustion or to electricity through fuel cells. However, hydrogen is a colorless, odorless, flammable gas with a lower explosive limit of 4% in air. Accordingly, in order to implement the safe manufacturing, distribution and use of hydrogen, sensors must be developed that can rapidly detect low levels of hydrogen for hydrogen gas leak detection.

BRIEF DESCRIPTION OF THE PRIOR ART

Significant effort has gone into the development of hydrogen sensors for application to leak detection, including development of methods that utilize metal and metal oxide films such as Ti, $TiO_2$, PtO, and Pt and combinations thereof. Some methods use biologically based enzyme catalyzed electrochemical detection. Such sensors have numerous drawbacks, including slow response time, lack of selectivity for hydrogen, poor reversibility, and the requirement of high temperatures for operation (often up to 200° C.) and even higher temperatures (up to 500° C.) for sensor regeneration. Much of the research effort has focused on palladium and palladium alloy films and nanostructures. It is well known that palladium is an ideal material for hydrogen sensing since it selectively absorbs large quantities of hydrogen. When palladium metal is exposed to hydrogen gas ($H_2$), the hydrogen dissociates at the metal surface and the hydrogen atoms diffuse into the bulk of the palladium. The hydrogen atoms eventually reach an equilibrium concentration in the palladium that is directly related to the concentration of hydrogen gas in the surrounding environment. The absorbed hydrogen interacts with the palladium to cause either an increase or a decrease in electrical resistance of the palladium, depending on the characteristics and morphology of the palladium structure in question. Thus, much of the hydrogen sensor research to date has focused on developing sensors with resistive elements whose resistance is dependent on hydrogen concentration. This change in resistance can be measured directly to determine the hydrogen gas concentration, or the change in resistance can be used to modify the performance of another device, such as a Schottky diode or a FET (CHEMFET). Mesoscale palladium wires have also been demonstrated for use as sensitive hydrogen sensing elements.

In thick film and bulk palladium, the palladium and hydrogen combine to form palladium hydride. This causes an increase in the resistance of the films relative to palladium, which can be related to the concentration of hydrogen. Another known phenomenon that occurs in palladium is called Hydrogen Induced Lattice Expansion (HILE). This refers to the tendency for the palladium lattice to swell or expand upon absorption of hydrogen. At room temperature, bulk $PdH_x$ (where x<0.8) undergoes an $\alpha$ to $\beta$ transition starting at between 1% and 2% hydrogen gas concentration at one atmosphere pressure. This lattice transition causes a change in the lattice constant from 3.895 Å to 4.025 Å, resulting in an increase in volume of roughly 11%. Palladium is suitable for wetting the surface of many materials, including bare glass. This means that in ultra thin evaporated palladium films, the palladium tends to spread out in clusters tens of nanometers across and separated by randomly distributed distances with some clusters very close together and some many tens of nanometers apart. In thicker continuous palladium films, wetting of the surface can create problems if the film is exposed to moderately high levels of and undergoes HILE. Due to stiction, or the inability of the palladium atoms to move on the substrate surface, HILE can introduce enough strain in the film to cause film separation from the substrate, leading to failure of the device.

Prior surface acoustic wave (SAW) based chemical vapor sensors utilize various chemically selective coatings to absorb vapors of interest and cause measurable changes in device performance. Most of the coatings utilized in such sensors are viscoelastic polymers, metal oxides, or similar films. Sensors reported to date utilize various changes in device performance as metrics that indicate vapor concentration. Previously described passive SAW chemical vapor sensors generally use either the resonance frequency of a SAW resonator (measured directly or derived using the Fourier Transform of the sensor impulse response), or the time delay of a SAW delay line (measured directly in an oscillator loop) as the parameter measured to determine vapor concentration.

Changes in device performance on vapor exposure have been attributed to a combination of factors. The primary change noted has been mass loading. As vapor molecules are absorbed into the film, mass is added to the surface, and a change in velocity is observed, resulting in a corresponding change in delay or resonant frequency for the sensor device. Amplitude can also vary for the device. Additional effects, which are secondary in most applications, are film stiffness and viscoelastic effects. Absorption of vapors into the film can cause a softening, or in some cases a stiffening, of the films. These changes, combined with changes in film viscosity, result in variations in device performance measurable as shifts in frequency and delay and changes in amplitude. The last potential mechanism for coating/vapor interactions to cause changes in device performance is the effect of electrical interactions. Absorption of chemical vapors by film coatings can result in a change in the dielectric constant of the film. While this has the potential to affect the device performance, this effect is insubstantial for low-coupling substrates and has generally been neglected in evaluating prior sensor device performance.

SUMMARY OF THE INVENTION

The present invention relates to devices and methods for monitoring the composition of gases, and more particularly, to solid state sensor devices and methods for measuring the concentration of hydrogen in a gas composition. Specifically, the invention relates to a novel passive surface acoustic wave (SAW) based hydrogen sensor utilizing palladium (Pd) nanocluster film elements formed on siloxane self-assembled monolayers (SAM) assembled on piezoelectric SAW device substrates. This combination produces fast, reversible, highly sensitive hydrogen sensors capable of detecting a wide range of hydrogen concentrations and operating at room temperature. The palladium nanocluster films experience large conductivity changes due to the hydrogen induced lattice expansion of the palladium nanoclusters, combined with the quantum nature of conduction in nanocluster films. The performance of the SAW device will change in response to a change in conductivity of this film.

Unlike prior SAW sensors, the devices according to the invention utilize changes in the electrical characteristics of this film, responding to a change in the conductivity of the palladium nanocluster film upon exposure to hydrogen. The preferred embodiments either utilize the piezoelectric shorting effect to create a change in surface wave velocity in response to a change in film conductivity, or use the change in impedance of the film elements to affect the electrical and acoustic properties of the SAW device.

The sensors of the current invention utilize self-assembled siloxane monolayers on the piezoelectric substrate to provide appropriate surface chemistry for deposition of the palladium nanocluster films. Recent work at Argonne National Labs on the formation of palladium nanocluster films on self-assembled siloxane monolayers on glass has delineated the benefits associated with the use of such SAM films. This work used a surface treatment that generates a self-assembled monolayer (SAM) of siloxane on glass substrates. The siloxane SAM creates a hydrophobic surface, and also makes it harder for palladium to wet the surface.

As a result, when ultra-thin palladium layers are evaporated onto glass slides coated with siloxane SAMs, the resulting film is composed of numerous small, fairly uniform palladium nanoclusters separated by small gaps. These films have a nominal resistance in the absence of hydrogen. Upon exposure to hydrogen, however, the HILE causes the palladium nanoclusters to swell. Due to the uniformity of the nanoclusters and their small separation distances, this swelling causes many more clusters to be closer to one another. Thus, more pathways for quantum mechanical electron tunneling conduction are formed within the film, and film conductivity goes up dramatically as hydrogen is absorbed. This effect has been shown to be fast, reversible, stable, and operable at room temperature. These optimized nanocluster films demonstrated hydrogen sensing from 25 ppm to over 2% hydrogen, with response times of milliseconds, complete reversibility, and no baseline drift at room temperature. Other surface configurations could be used in place of the siloxane SAM to provide a surface that palladium would not wet well, and that would encourage the formation of appropriately sized and uniformly distributed palladium nanoclusters.

Such palladium nanocluster films, when deposited on properly surface-treated piezoelectric SAW substrates (i.e. with siloxane SAM coatings), produce films with hydrogen-dependent electrical properties. Of course, the absorption of hydrogen by these films also causes a small response due to mass loading of the hydrogen. This effect, however, is much smaller than the piezoelectric shorting effect observed, provided the piezoelectric substrate being used is a high coupling ($k^2$) material such as lithium niobate, lithium tantalate, langasite, or other high coupling material.

Thus, if a palladium nanocluster film is deposited on the surface of a piezoelectric substrate such as lithium niobate, a change in velocity $\Delta v/v$ occurs due to the electrical nature and mass loading of the film. Using published dispersion curves for gold films on lithium niobate, $\Delta v/\Delta(hk)=2600$ m/sec for gold (between 2300 and 2600 m/sec), where h is the thickness of the film in angstroms and k is the wave number ($k=2\pi/\lambda$). If it is assumed that the SAW device operates at 750 MHz, then $\lambda=4.5$ μm, and $\Delta v/\Delta h=3.6\times10^9$ sec$^{-1}$. This provides a measure of the added change in surface wave velocity ($\Delta v$) due to a small increase in film thickness ($\Delta h$) for the gold film. If one assumes that the additional film thickness is $\Delta h=3.3$ nm (the optimal palladium nanocluster film thickness determined by the work at Argonne), then for an ultra thin (3.3 nm) gold film, the change in velocity due to the added mass is $\Delta v_{Au\ mass}=12$ m/sec.

Now, considering the fact that the mass density ratio of palladium to gold is 12,000/19,300=0.62, the velocity change due to the Palladium film is calculated as $\Delta v_{Pd\ mass}=7.5$ m/sec. This velocity shift is the velocity shift that occurs due to mass loading and electrical effects when the palladium film is deposited, and not a shift that is indicative of the velocity shift when the palladium absorbs hydrogen. Using the same dispersion curves, one can estimate the mass change that this 3.3 nm palladium film will experience due to absorption of hydrogen. It has been reported that palladium absorbs six times its volume in hydrogen. Assuming this to be true, one can determine the velocity change due to the added mass of the hydrogen. Taking the ratio of the mass density of hydrogen to the mass density of palladium (0.085/12,000=7.08×10$^{-6}$), and multiplying by six (since palladium can absorb six times its volume in hydrogen gas), the palladium film will experience an additional velocity shift due to the absorbed hydrogen mass of 4.25×10$^{-5}$ times the velocity shift due to palladium mass loading. Since this was previously found to be $\Delta$vpalladium mass=7.5 m/sec, we can see that the additional mass loading due to the absorbed hydrogen is $\Delta v_{H\ mass}=(7.5\ m/sec)\times4.25\times10^{-5}=0.00032$ m/sec.

By comparison, the $\Delta v/v$ caused by electrical shorting of the surface wave on lithium niobate is 2.5%. This corresponds to a change from an open circuited surface to a short circuited surface. Since the palladium film will have some nominal conductivity, the surface with no hydrogen exposure will not be purely open circuited. Although the film conductivity at the surface of the device should increase with increasing hydrogen exposure, it may not reach a true short circuit. Still, if one assumes that the $\Delta v/v$ achievable with hydrogen exposure using these films is only $\frac{1}{10}$ of the ideal value, that still corresponds to a change of $\frac{1}{10}\times(\Delta v/v)$ =0.25%, which yields $\Delta v_{elec}=3400$ m/sec (0.0025)=8.5 m/sec. Comparing the magnitude of these two effects, we see that $\Delta v_{elec}/\Delta v_{H\ mass}=26,600$. Thus, the change caused by mass loading due to hydrogen absorption is less than 0.004% of the change due to electrical shorting effects. That is, the effects caused by changes in electrical properties of the palladium nanocluster film upon exposure to hydrogen far outweigh the mass loading effects of the hydrogen.

Knowing the advantages provided by the use of a siloxane SAM and the palladium nanocluster film, numerous embodiments of the present invention are possible, including resonant SAW structures, delay line and differential delay line structures, coded and non-coded devices, tag devices, and devices incorporating tapered and stepped tapered transducers and reflectors.

BRIEF DESCRIPTION OF THE FIGURES

Other objects and advantages of the invention will become apparent from a study of the following specification when viewed in the light of the accompanying drawing, in which.

DETAILED DESCRIPTION

Figure 1:
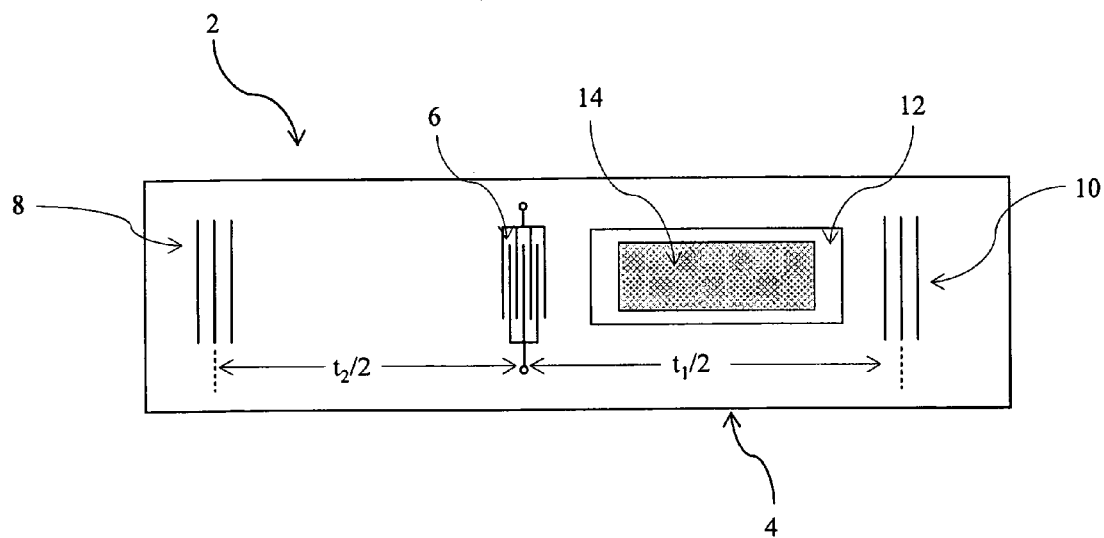
FIG. 1 is a top view of a hydrogen sensor device according to the invention.

Referring first to FIG. 1, there is shown a differential delay line device 2 for detecting the presence of hydrogen according to the present invention. The device includes a piezoelectric substrate 4 on which is mounted an input surface acoustic wave (SAW) transducer 6 in the center region thereof and two (SAW) elements such as reflectors 8, 10 at opposite ends of the device. A self-assembled siloxane monolayer 12 is arranged over a portion of one of the propagation paths between the transducer and one of the reflectors 10 and layer of palladium film 14 is arranged as a nanocluster film on the monolayer 12. The device uses the change in velocity caused by the shorting effect of the palladium film as hydrogen is absorbed, thereby to increase the delay on one side of the device. Although the transducer is shown in the center with the reflectors at opposite ends of the device, other arrangements may be used as well.

Figure 2:
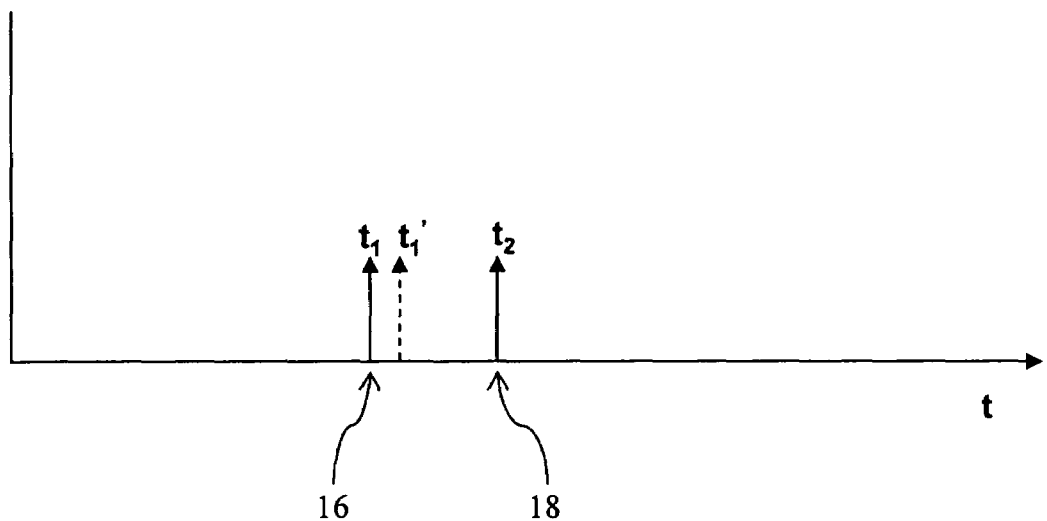
FIG. 2 is a graphical representation of the idealized impulses from the sensor of FIG. 1.
Figure 3:
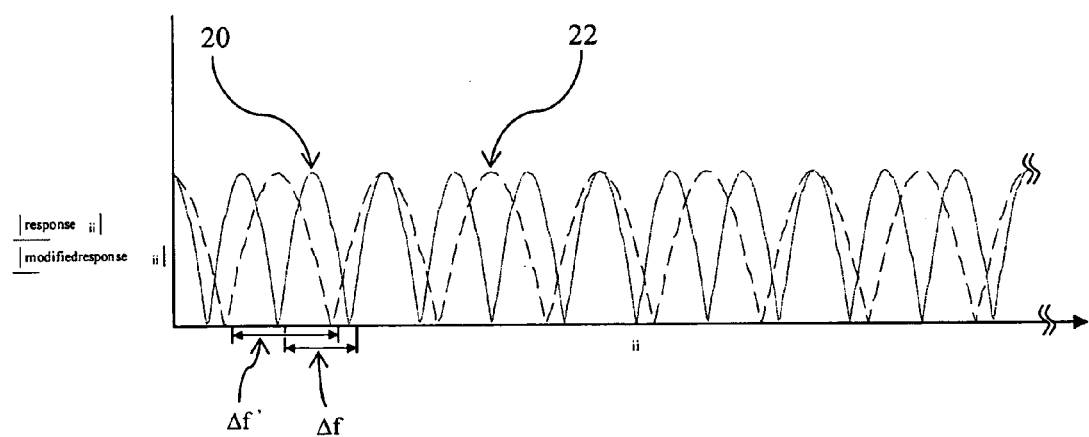
FIG. 3 is a graphical representation of the idealized frequency response for the sensor of FIG. 1.

Taking the input transducer to be broadband, and treating the reflector elements 8, 10 at either end as ideal point reflectors, the time domain reflected response resulting from interrogation of the device is a pair of impulses 16 and 18 shown in FIG. 2 at times $t_1$ and $t_2$. These times correspond to the round trip delay times of a surface wave as it travels from the input transducer 6 to the reflectors 8, 10 and back to the input transducer. The corresponding frequency response is a lobed response, shown by the solid lines 20 in FIG. 3. The frequency separation between nulls of this lobed response is given by $\Delta f=1/(t_2-t_1)$. As shown on the FIG. 3, the $\Delta f$ can be quite large. For example, if $t_1=1.000$ μsec and $t_2=1.010$ μsec, then $\Delta f=1/(0.01 \text{ μsec})=100$ MHz.

Absorption of hydrogen by the palladium nanocluster film 14 results in a change in film conductivity, which causes an increased electrical shorting of the surface. Since the velocity of the wave slows down as the surface is shorted, absorption of the hydrogen leads to a change in the delay $t_1$ to a new longer delay $t_1'$. For example, it can be assumed that this shorting effect causes a change in surface wave velocity equal to approximately 1/10 of the total possible Δv/v for shorting on the substrate. Using YZ lithium niobate as the substrate, which has Δv/v=2.5%, then $t_1'=t_1+(0.0025*1$ μsec$)=1.0025$ μsec. Since $t_1'$ will actually be longer than $t_1$ which will result in a shrinking of the separation between the impulses, i.e. $(t_2-t_1')<(t_2-t_1)$, the lobes spread in frequency, which as shown by the dotted lines 22 in FIG. 3, results in a corresponding spreading of the separation between the nulls of the lobed frequency response. The change in frequency for the lobe 20 when it spreads is related to the fact that the width of the spread lobe 22 is greater than the width of the un-spread lobe 20, or $\Delta f'=1/(t_2-t_1')>\Delta f=1/(t_2-t_1)$. In this example $t_2-t_1'=1.010$ μsec$-1.0025$ μsec$=0.0075$ μsec. Thus while $\Delta f=1/(0.01 \text{ μsec})=100$ MHz, $\Delta f'=1/(0.0075 \text{ μsec})=133$ MHz. Since the lobe width Δf changes by 33 MHz for each frequency lobe, lobes that are farther out in frequency are both shifted in frequency and broadened by this effect. Thus, the locations of the nulls for lobes farther out in frequency change will change even more. This is a very large effect, and can be measured using a time-integrating correlator-based interrogator system. It should be noted that since the change in lobe width due to hydrogen absorption depends on the nominal delays and the amount of shorting achieved in the palladium film, this structure of the device 2 can be designed to provide the sensitivity desired.

Now, it has been shown (using photosensitive CdSe semiconductors on $LiNbO_3$) that the propagation of surface waves in high coupling substrates such as lithium niobate can be affected by the conductivity of the layer placed on the device surface. For high conductivity layers of CdSe (when photoelectrically activated), the carriers in the semiconductor can move along without much resistance, and therefore there is no drag on the acoustic wave. At low film conductivity, there are not enough carriers in the CdSe film to interact with the surface wave to cause drag. In the range of moderate conductivity, however, the interaction of the surface wave with the semiconductor causes drag on the surface wave, where limited carrier mobility actually causes a dip in the amplitude of the observed response as energy is being used to transport the charge carriers in the semiconductor. It is possible that such an effect may be observed in the palladium nanocluster films of the present invention, but proper design can avoid this being a problem.

The movement of the lobes of the sensor due to absorption of hydrogen by the palladium film can be on the order of tens of Megahertz with relatively small changes in conductivity. An interrogator can be used to measure the shifting of these lobes as will be discussed in greater detail below.

A second embodiment of the current invention utilizes resistive elements formed from the palladium nanocluster films to control the performance of the SAW device in such a way as to vary the device response with exposure to hydrogen. Such an embodiment will now be described with reference to FIG. 4. A piezoelectric substrate 24 has an input transducer 26 and two reflective structures 28 and 30 formed on a surface thereof. Each reflective structure is subdivided into separate portions 28a, 28b and 30a, 30b. A variable resistance element 32, 34 is connected with each reflective structure. An example of a variable resistance element is shown in FIG. 5. Each variable resistance element is formed from a palladium nanocluster film 36 formed in a pattern on a siloxane SAM 38. The SAW device of FIG. 4 utilizes regeneration reflections and thus uses split finger electrodes. Without hydrogen present or with hydrogen present at low background levels, the reflectors 28, 30 each have a predetermined center of reflection. When higher levels of hydrogen are encountered, the palladium film absorbs the hydrogen, and the resistance of the variable resistance elements 32, 34 goes down. At high enough conductivities, these sections are electrically shorted. The level of regeneration reflection will go down with increased shorting, ultimately resulting in no regeneration reflection from these sections. This causes a shift in the center of reflection of these devices, with reflector 28 moving away from the input transducer 26 and reflector 30 moving closer to the input transducer 26. This leads to a change in the time difference of the reflected responses and to a change in the output lobe shape. Such a change can be detected using the time integrating correlator approach described above.

A further embodiment of the invention uses SAW devices with arbitrary coding techniques such as PN, MSK, barker, FSK, OFC, in-phase and quadrature (I/Q) or other coding, in addition to the siloxane SAM and thin palladium nanocluster films described above. In the following description, a specific implementation of OFC is used by way of example only to demonstrate the range of possible embodiments for the device. However, as will be appreciated by those of ordinary skill in the art, the embodiments discussed could also be implemented using any other known coding techniques. Additionally, it is understood that such coded sensors can be implemented using transduction effects rather than reflection effects, and that the coding can be placed in either the launching transducer or the outer transduction or reflection elements, at the selection of the designer.

Figure 6:
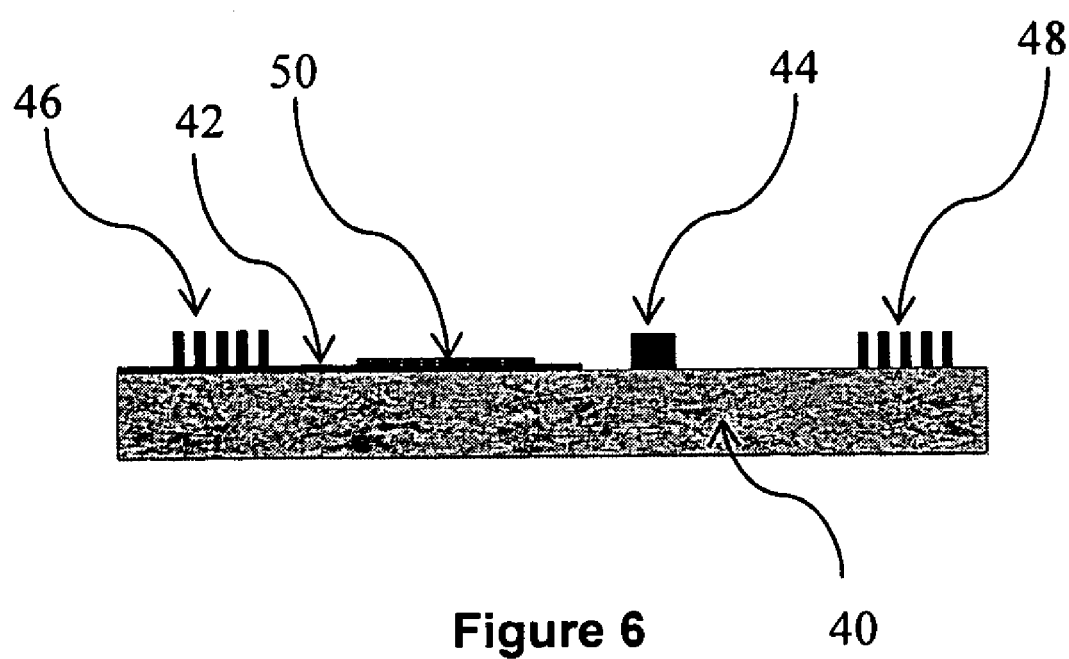
FIG. 6 is a side view of an alternate embodiment of a hydrogen sensor using orthogonal frequency coded reflectors according to the invention.

Orthogonal Frequency Coded (OFC) SAW devices have been used as passive wireless temperature sensors. This particular embodiment of these devices utilizes central launching and receiving transducers, and reflective arrays of orthogonal elements to generate a code in the devices. One simple embodiment of an OFC hydrogen sensor would be to place a nanocluster film on one side of the differential delay line, similar to the embodiment shown in FIG. 1, but causing a hydrogen sensitive shift in the delay difference between the two compressed pulses in the receiver. Such a change would be measured by the OFC interrogator. Such a configuration is shown schematically in FIG. 6.

More particularly, the device includes a piezoelectric substrate 40 having a siloxane SAM layer 42 applied to a surface thereof. This SAM may extend over the entire substrate (under transducer and reflector structures) as shown for the left reflector of FIG. 6 or may be limited to the region of the device with the palladium nanocluster film. An input transducer 44 is mounted on the piezoelectric substrate with OFC reflectors 46 and 48 mounted on opposite sides of the transducer toward the edges of the substrate. A palladium nanocluster film layer 50 is provided on the SAM layer between the transducer and one of the reflectors.

Other alternate OFC device embodiments are within the scope of the invention. For example, OFC or other coding can be incorporated into the central launching and receiving transducer, and transducers can replace the outer reflectors. In this instance, the outer transducers can be electrically connected to the input transducer and antenna, or can be separate, depending on the device function desired. This configuration results in a device response that is a transduction response, rather than a reflective response. Alternate embodiments using either this approach or the reflective approach use multiple tracks on a single substrate, or multiple parallel devices on separate substrates. Each track comprises an OFC differential delay line. The non-hydrogen sensing track will serve as a reference temperature sensor for the pair or set of sensors. For the hydrogen sensitive track(s), however, either a palladium nanocluster film element is deposited in the differential delay region (if the differential delay line approach is used), or selected OFC reflector chip elements are modified to include split electrodes ($\lambda/8$ wide), separate bus bars, and a palladium nanocluster resistive element (if the reflective approach is used). The form and geometry of this element is determined based on impedance characteristics of the films and device.

In current OFC devices, the reflective sections that form the chips of the OFC code are implemented using non-split electrodes ($\lambda/4$ wide) in electrically shorted configurations. Since these reflective structures are electrically shorted, they exhibit no electrical regeneration reflections, the strongest component of reflection possible on high coupling substrates like lithium niobate. Instead, these reflectors use the electrical shorting reflections and energy storage reflections at the finger edges to generate the reflected wave. The proposed hydrogen sensitive devices would use only the electrical regeneration reflection mechanism for reflecting the surface wave. When an incident surface wave impinges on a set of periodic, electrically non-shorted electrodes, a voltage is induced on the electrodes. This voltage, in turn, generates an acoustic wave in the opposite direction (the regeneration reflection).

When the reflector sections include split electrodes, the geometry of the device causes all reflections due to mass loading, energy storage, and piezoelectric shorting effects to cancel, leaving wave regeneration as the only reflection mechanism. If a variable resistance is connected across a section of the reflector, controlling this resistance will control the reflection from this section. For instance, if one chip of the OFC code has its bus bars connected with a palladium thin film resistor, and the resistor has a high impedance, then the section is essentially open circuited, and regeneration reflections will occur as normal. Should the palladium resistor absorb hydrogen, however, the dramatic increase in conductivity will short the bus bars, eliminating the regeneration reflection from this section of the reflector. This type of "switching" can result in selected portions of the OFC code being reduced or eliminated. It may be possible to make the resistive elements attached to different portions of the reflector have different characteristics, so that selected portions of the OFC code respond to different levels of hydrogen. Or, it may be possible to quantify the hydrogen level based on the degradation in sensor response. Portions of the OFC code in the hydrogen sensing track would be left intact to verify continued device operation. This embodiment would use an interrogator as described below, but modified to take into account the anticipated changes in OFC device response due to hydrogen exposure.

Figure 7:
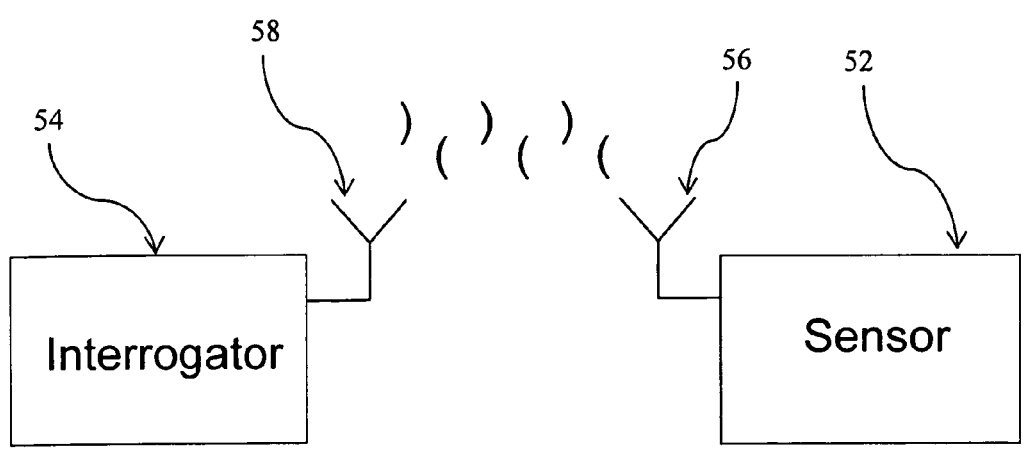
FIG. 7 is a block diagram of a hydrogen sensing system according to the invention.

The invention also relates to a system for hydrogen sensing in which a signal from a hydrogen sensor is processed to produce an indication of hydrogen concentration. Such a system is shown in its broadest configuration in FIG. 7 where a hydrogen sensor 52 such as that of FIG. 1 provides a response signal to an interrogator 54 which processes the response signal. The sensor includes an antenna 56 and the interrogator includes an antenna 58 for wireless transmission and reception of signals therebetween. Alternatively, a wired connection may be provided between the sensor and interrogator as is known in the art.

Figure 8:
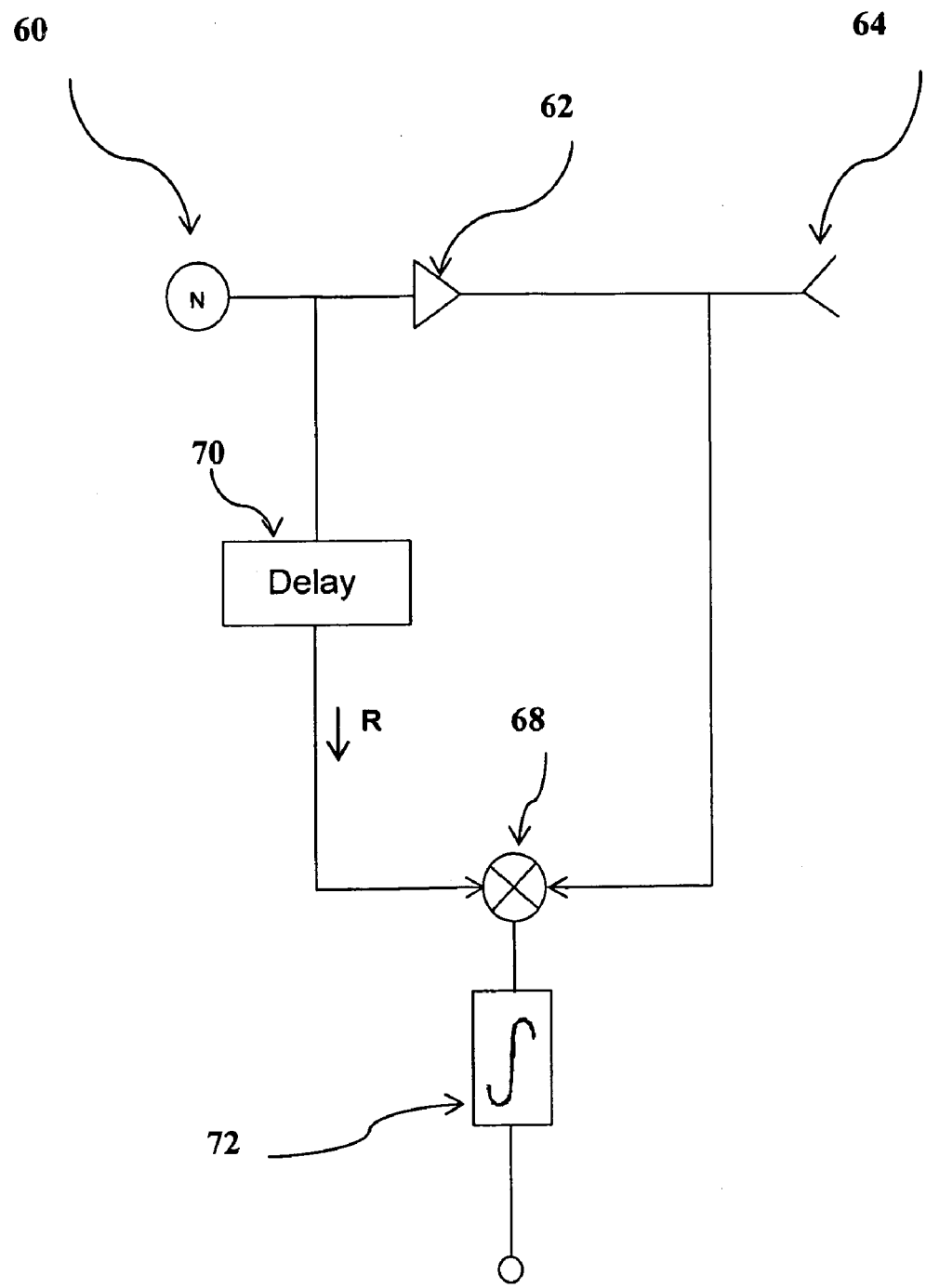
FIG. 8 is a circuit diagram of a time-integrating correlator interrogation system according to the prior art.

A first embodiment of an interrogator circuit for detection of lobe shift using a time integrating correlator is shown in FIG. 8. A wide band noise source 60 supplies an output voltage signal. This signal is amplified by an amplifier 62 and supplied to an antenna 64 for transmission. The transmitted signal is received by a target or sensor and reflected back to the antenna 64. The amplifier 62 blocks the returned signal from going back to noise source 60, but the return signal is applied to one of the input ports of a multiplier 68. While passing from the noise source 60 to the antenna 64, propagating to the target, and returning to the antenna, the signal experiences a delay T. The signal reflected from the target and delivered to the right side input of the multiplier is the interrogation signal I.

The same noise signal which is the source of the interrogation signal is delivered to a delay line 70 where it is delayed. The delayed signal, which is a reference signal R, is applied to the other input of the multiplier 68. The reference signal and the interrogation signal travel different paths to the multiplier 68 but both have experienced the same delay. Therefore, assuming that the target is an ideal reflector, then except for different amplitude levels, the two signals are identical regardless of the nature of the noise source. The signal at the output of the multiplier 68 is thus the product of identical signals or the square of the noise signal. The square of any voltage is a positive number. This output is delivered to an integrator 72 whose output is a constantly increasing value. The output signal is a low level signal that has experienced significant attenuation, particularly in the path to the target and back. But the integration of this low level DC signal offset results in significant signal levels due to the large amount of processing gain. As a typical example, if the noise bandwidth of the signal at the multiplier is 200 MHz and the effective integration time of the integrator is 10 milliseconds, then the processing gain is 2,000,000 or 63 dB. This can be regarded as a direct amplification of the information signal with respect to the noise signal. The output of this simple circuit cannot provide any information of the sensor measurand, but it provides an approach for interrogating a passive sensor with enormous processing gain. The operation of a time integrating correlator capable of large processing gain is well known in the field of signal processing.

The noise source 60 may be a white noise generator or it can be a pseudo noise generator (i.e., PN code generator) or any other wide band signal generator. A SAW delay line is suitable for the delay 70 and a diode or diode array may serve as the multiplier 68. An RC circuit serves well as the integrator 72. The time constant of the RC circuit is the effective integration time.

Figure 9:
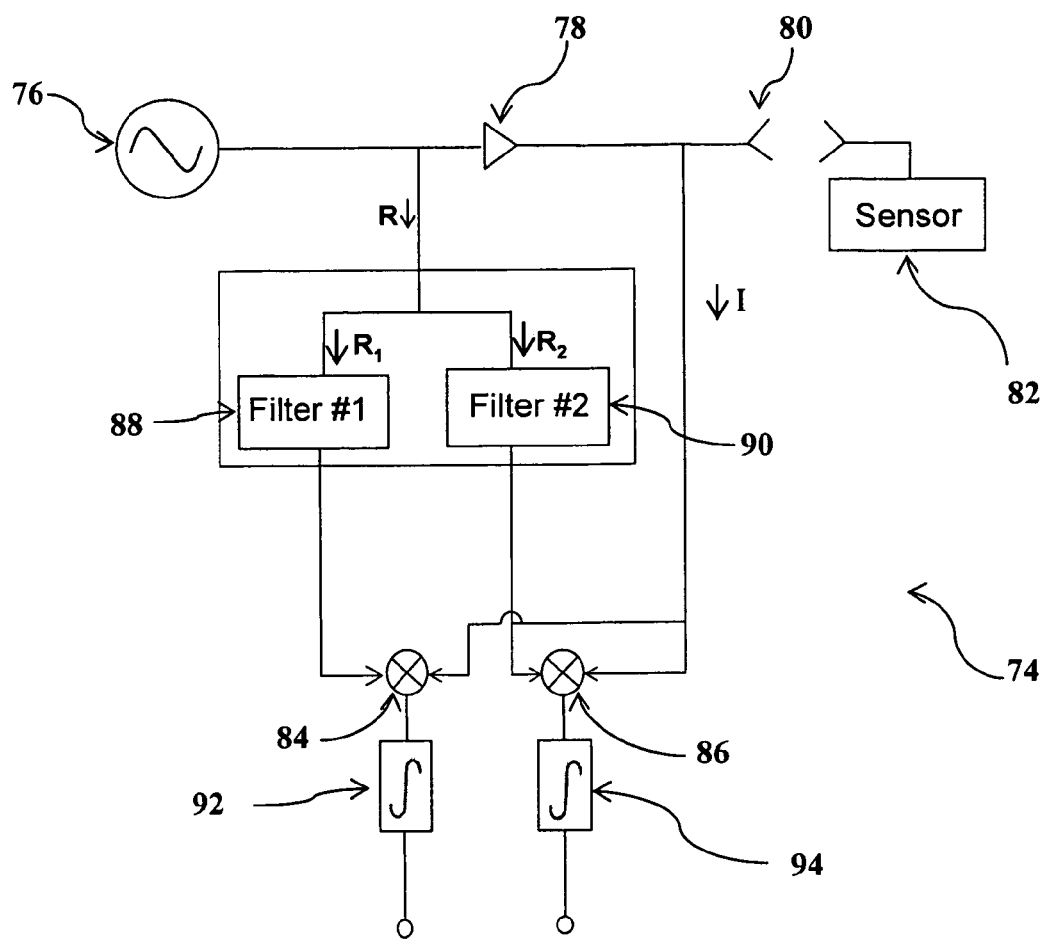
FIG. 9 is a circuit diagram of a hydrogen sensing system according to the invention.

FIG. 9 shows an embodiment of the present invention in which a system 74 that can measure hydrogen concentration uses a sensor as described above with reference to FIG. 1. A noise source 76 delivers a reference signal to an amplifier 78. The reference signal is amplified to produce an interrogation signal which is delivered to an antenna 80 for transmission to a hydrogen sensor 82 such as that shown in FIGS. 1 or 4. The interrogation signal interacts with the sensor and is reflected back to the antenna 80. Before being transmitted to the sensor, the frequency power density is flat. The returning interrogation signal I is applied to the right input ports of multipliers 84 and 86. A reference signal R is filtered and delayed by filters 88 and 90 and is applied to the left input ports of the multipliers 84 and 86, respectively. The delays through the two filters are set to be equal to the delay through the interrogation path. Thus, at each frequency the interrogation signal I at the antenna is identical in phase and delay to the reference signal R with amplitude modified by the sensor. Thus, the output of multiplier 84 is the square of the noise signal component (i.e., positive dc level) times the product of the spectral levels. Accordingly, the baseband signal level at the output of the multiplier 84 is the product of the reference signal R1 from the first filter 88 and the interrogation signal I. The baseband signal level at the output of the multiplier 86 is the product of the reference signal R2 from the second filter 90 and the interrogation signal I. Integrators 92 and 94 are connected with the outputs of the multipliers 84 and 86, respectively. The integration process integrates the curves over frequency and then integrates over time according to the time constant of the RC integration circuit. In the case where the sensor is not exposed to hydrogen (and ignoring temperature effects), the outputs of the integrators are equal, and the ratio of the output levels is 1.0. As the hydrogen concentration changes, the frequency response of the sensor shifts due to the changing lobe widths. This results in more energy in one output and less in the other, as will be described in greater detail below, which results in a change in the ratio of the outputs. This ratio is the parameter that indicates the hydrogen concentration. A lookup table can be established or a proportionality can be established between this ratio (the output ratio) and hydrogen concentration. This description assumes no changes in sensor performance due to temperature changes. Actual systems may require reference sensors to determine temperature along with hydrogen sensors, in order to take into account both effects.

Figure 10:
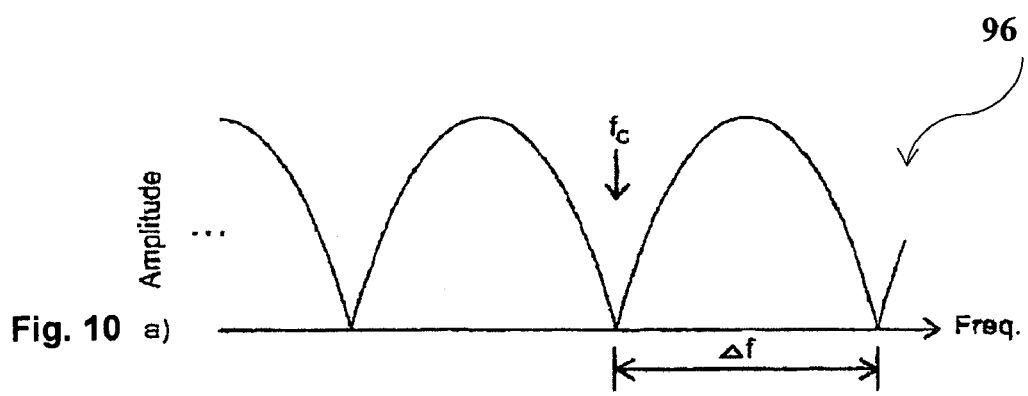
FIG. 10a is a graphical representation of the frequency response of the system of FIG. 9 at ambient temperature with only background hydrogen present.
FIG. 10b is a graphical representation of the frequency responses of the filters of the system of FIG. 9.
FIG. 10c is a graphical representation of the frequency responses at the outputs of the multipliers of the system of FIG. 9.
Figure 10:
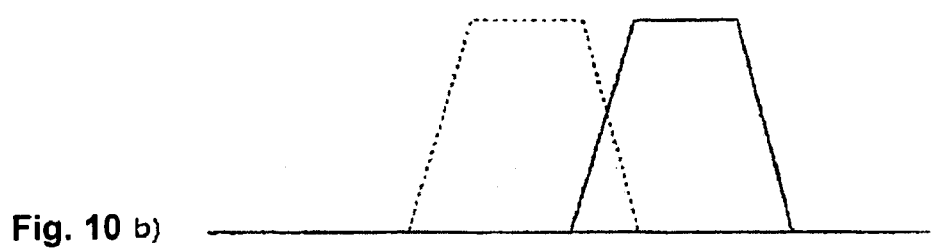
Figure 10:
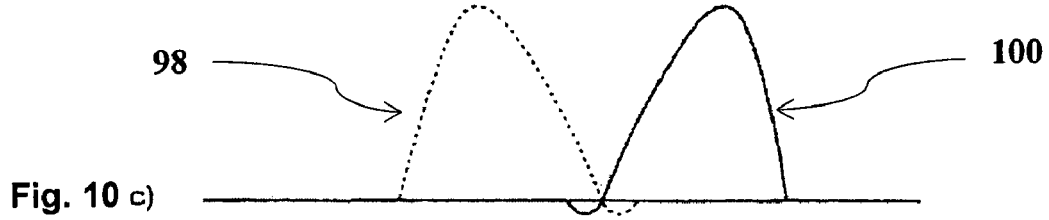
Figure 11:
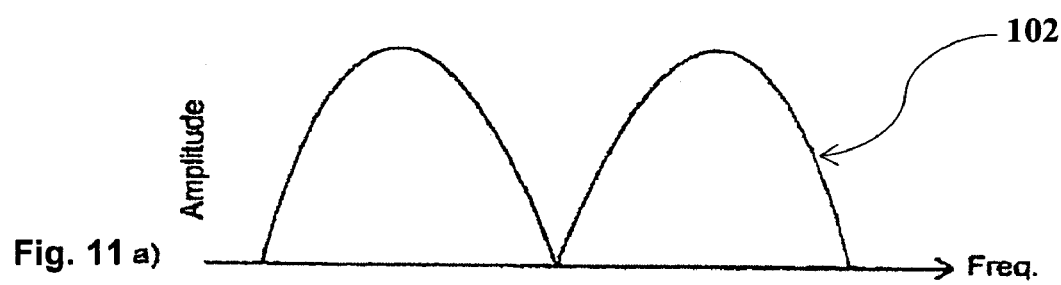
FIGS. 11a-c show frequency responses similar to FIGS. 10a-c, respectively, for a hydrogen sensing system of FIG. 9 when the system is exposed to hydrogen.
Figure 11:
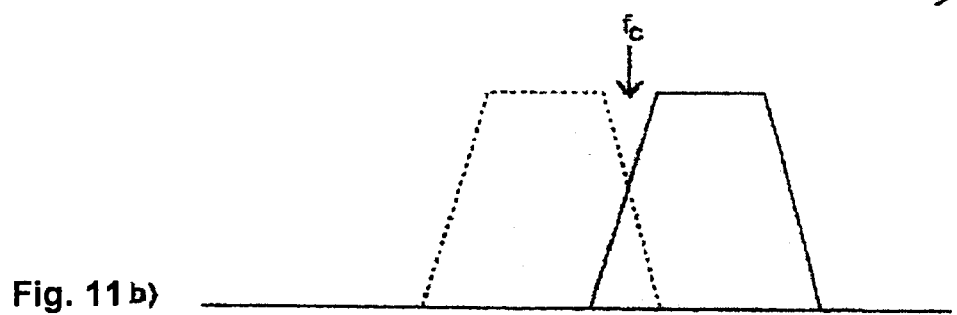
Figure 11:
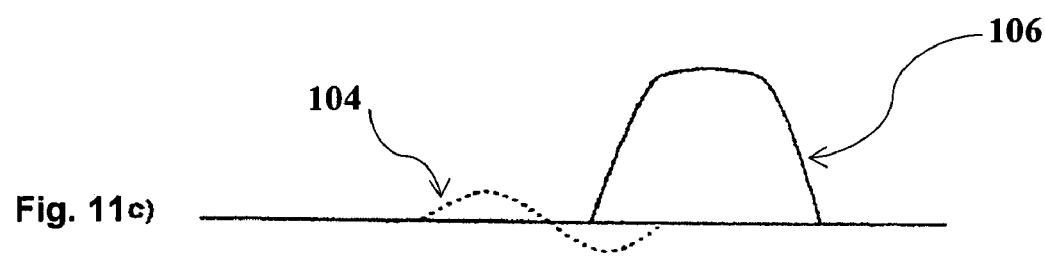

FIGS. 10 and 11 show how this change in sensor response, due to hydrogen exposure, is measured in the frequency domain. FIG. 10a shows the frequency response 96 of the sensor at ambient temperature and with only background hydrogen present. The location of one of the nulls is defined as $f_c$ and the spacing between nulls is $\Delta f$. FIG. 10b shows the frequency responses of the two filters 88 and 90 shown in FIG. 9. These responses cross at $f_c$. After being reflected back from the sensor, the power density is the lobed response 96 of FIG. 6a. The spectral power densities at the left inputs to the multipliers 84 and 86 are shown in FIG. 10b as the dotted 98 and solid 100 lines, respectively. Accordingly, the baseband signal level at the output of the multiplier 84 shown as the dotted line 98 in FIG. 10c is the product of FIG. 10a times the dotted line from the output of the multiplier 84 as shown in FIG. 10b. The integrated outputs are the integration of curves 98 and 100 of FIG. 10c, respectively.

The hydrogen sensor device can be designed so that the differential delay will increase, rather than decrease upon exposure to hydrogen. This is possible if the palladium film 14 in FIG. 1 is located between the input transducer 6 and reflective element 10 in the region corresponding to delay $t_2$. In this case, when the sensor is exposed to a change in hydrogen concentration, $t_2$ will increase. Referring now to FIG. 11, this causes the lobes of the frequency response to narrow, effectively shifting the location of the nulls of the lobes 102 being evaluated closer to baseband, since the shift is cumulative and increases as frequency increases—i.e. for nulls further away from baseband. The choice of lobe narrowing or broadening with exposure is arbitrary, as either case can work, and this selection can be controlled through sensor device design. The reference signal through filters 88 and 90 of FIG. 9, however, is not shifted and the filter responses still cross at frequency $f_c$ as before. The outputs of the multipliers 84 and 86 are shown in FIG. 11c as signals 104 and 106, respectively. The signal at the output of the multiplier 84 consists of two lobes of opposite sign so that when they are integrated over frequency they are subtracted and can in fact cancel. The integrated output of the integrator 92, therefore, is small. The integration of the signal at the output of the multiplier 86 shown as 106 in FIG. 11c is larger. The ratio of the voltages at the outputs of the integrators 92 and 94 is a large number which can be associated with a specific hydrogen level. The absolute value of the voltages at these outputs will vary with integration time and with reflection loss from the sensor, but as these effects are common to the paths of the two signals, the ratio between these voltages will not be affected by these variations and so will be an accurate indicator of hydrogen concentration.

Figure 12:
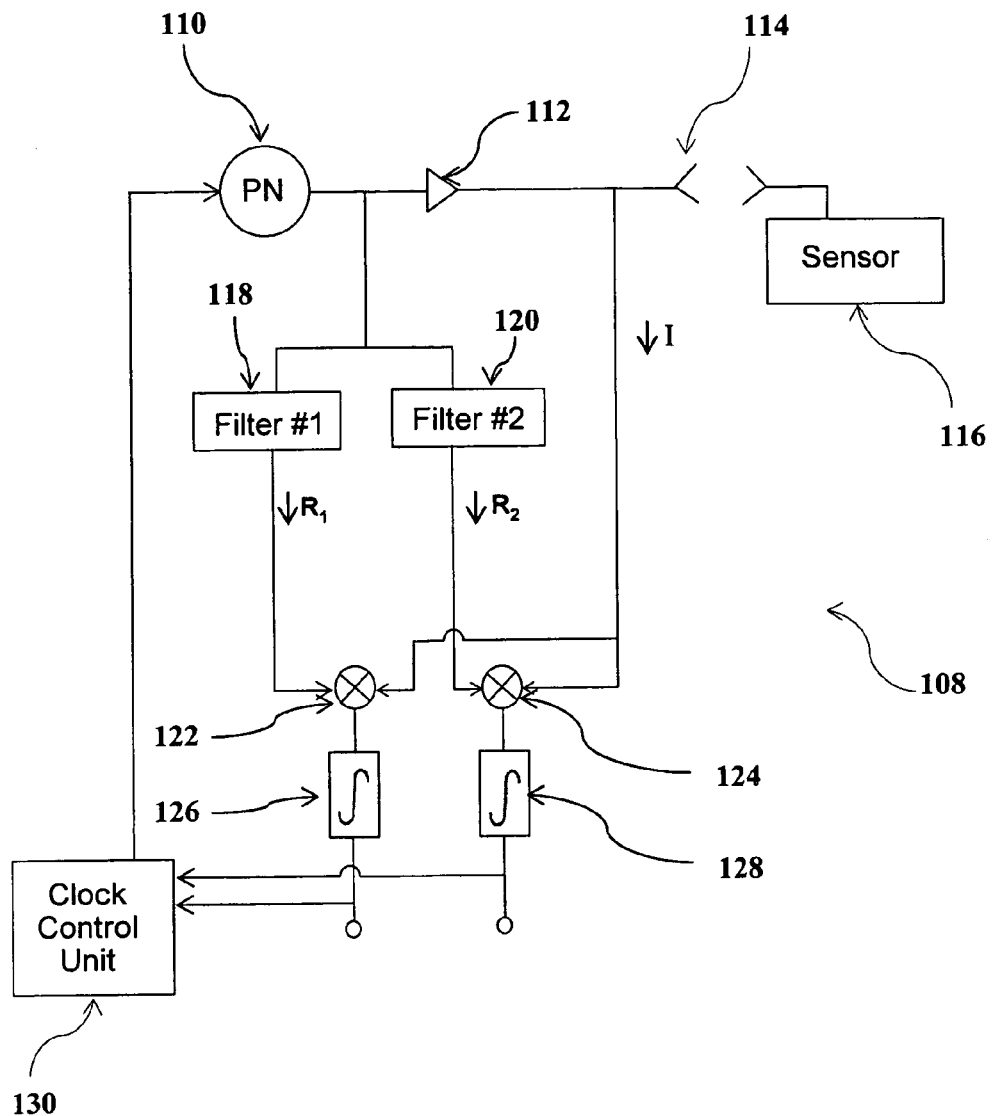
FIG. 12 is circuit diagram of a further embodiment of a hydrogen sensing system according to the invention wherein a pseudo-noise source is used as the signal source and a clock control unit is used to modulate the periodicity of the signal source.

FIG. 12 illustrates an alternate embodiment for an interrogator according to the present invention. In the embodiment discussed above, the interrogation and reference paths were designed to be equal. While this can be done, it is very difficult to achieve and even more difficult to maintain, since the sensor time delay is dependent on temperature and hydrogen concentration. What is needed is a means of dynamically varying the delay of one of the paths so that the delays can be held equal. The process of matching the delays in the interrogation and reference paths can be accomplished by replacing the white noise source with a source which has a noise power spectrum similar to white noise but that is periodic in time. One class of signals that has these properties is pseudo noise (PN) codes. These codes are well known in the field of signal processing. A PN code consists of a sequence of M bits which repeat indefinitely, where $M=2^N+1$ and N is any integer. Each bit can assume a value of +1 or −1. An RF signal modulated by a PN code is an example of a noise source that would suffice.

Figure 4:
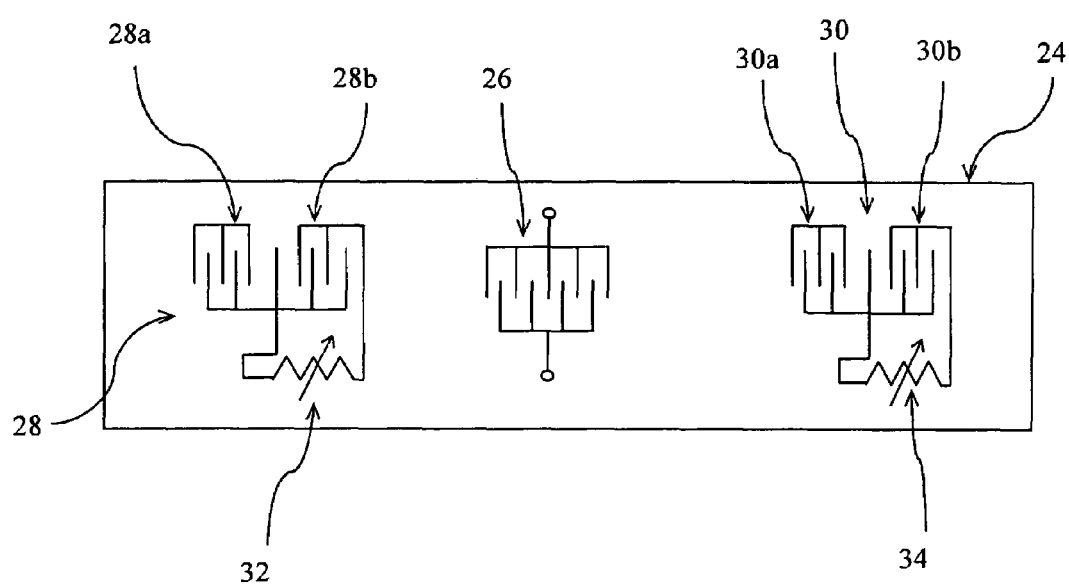
FIG. 4 is a top view of an alternate embodiment of a hydrogen sensor using variable resistance elements according to the invention.
Figure 5:
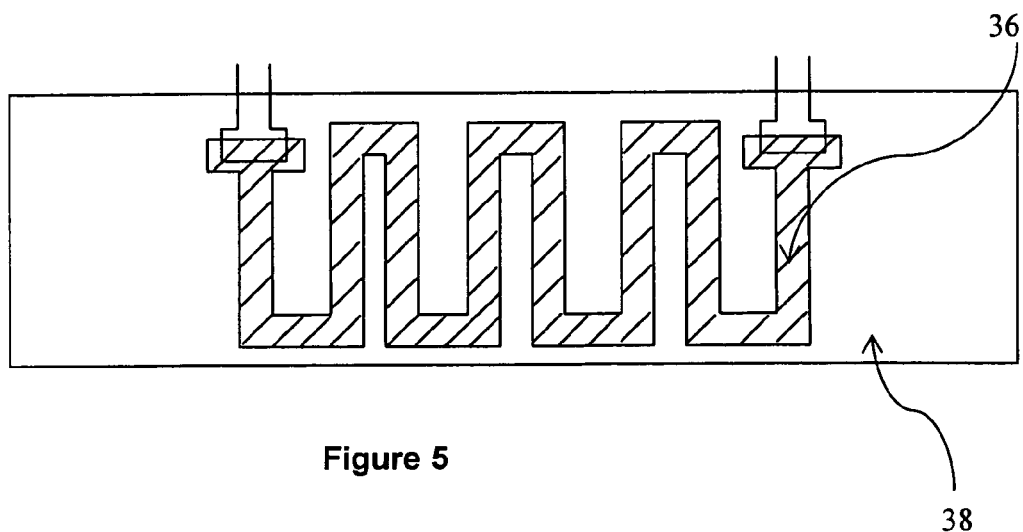
FIG. 5 is a detailed view of a variable resistance element of FIG. 4.

In the system of FIG. 12, a PN noise source 110 is provided which delivers a signal to an amplifier 112 for amplification prior to transmission by an antenna 114 to a hydrogen sensor 116 such as that shown in FIGS. 1 or 4. The noise signal is also delivered to first and second filters 118 and 120 which produce reference signals R1 and R2. As in the above embodiment, an interrogation signal I is generated by the reflected signal from the sensor. The interrogation and reference signals are sent to multipliers 122 and 124 whose outputs are sent to integrators 126 and 128.

One benefit of this alternate embodiment is that it is not necessary to implement a delay in the reference path to match the delay in the interrogation path, but rather the signal in the reference path can be shifted by one (or more) integral code lengths. In this manner the signals applied to the inputs of the multipliers can line up exactly, even though their delay paths differ by integer multiples of a full code length. The signals will not automatically line up since the delays can change with hydrogen concentration, position, and temperature, but there is an additional control by a clock control unit 130 connected between the outputs of the integrators 126 and 128 and the input of the PN noise source 110. If the bit rate is varied, the time length of the code changes. The code sequence remains the same, but the length of the code increases or decreases, i.e., scales with time as the clock rate is varied. In fact the clock rate or bit rate defines an effective delay between interrogation and reference signals which corresponds to a particular temperature, so that by varying the clock rate to maximize the total signal from the integrators, the corresponding clock rate will be a direct measurement of the temperature. The ratio of the outputs of the integrators 126 and 128 is the measurement of the hydrogen concentration.

The clock rate is adaptively varied by the system (clock control unit) to maximize the sum of the voltages at these outputs. This insures that the delay in the sensing path and the effective delay in the interrogation paths are in fact always equal. As long as this condition is met, i.e., the two delays being equal, clock rate is a metric which is affected by the absolute time delay in the interrogation path, which is dominated by T*TCF (where T is the temperature at the sensor and TCF is the temperature coefficient of frequency) and thus defines the temperature. On the other hand the ratio of the outputs is affected by the differential delay on the sensor and thus defines the hydrogen concentration. It is highly useful to provide temperature information concurrently with the hydrogen concentration because the dynamics of the interaction between the hydrogen and the palladium film are temperature dependent.

Additional aspects of the interrogator system that would be considered within the scope of this invention include adaptation of the system for operation with multiple sensors and providing coding in the sensor device and in the interrogator for identification of specific sensors.

Figure 13:
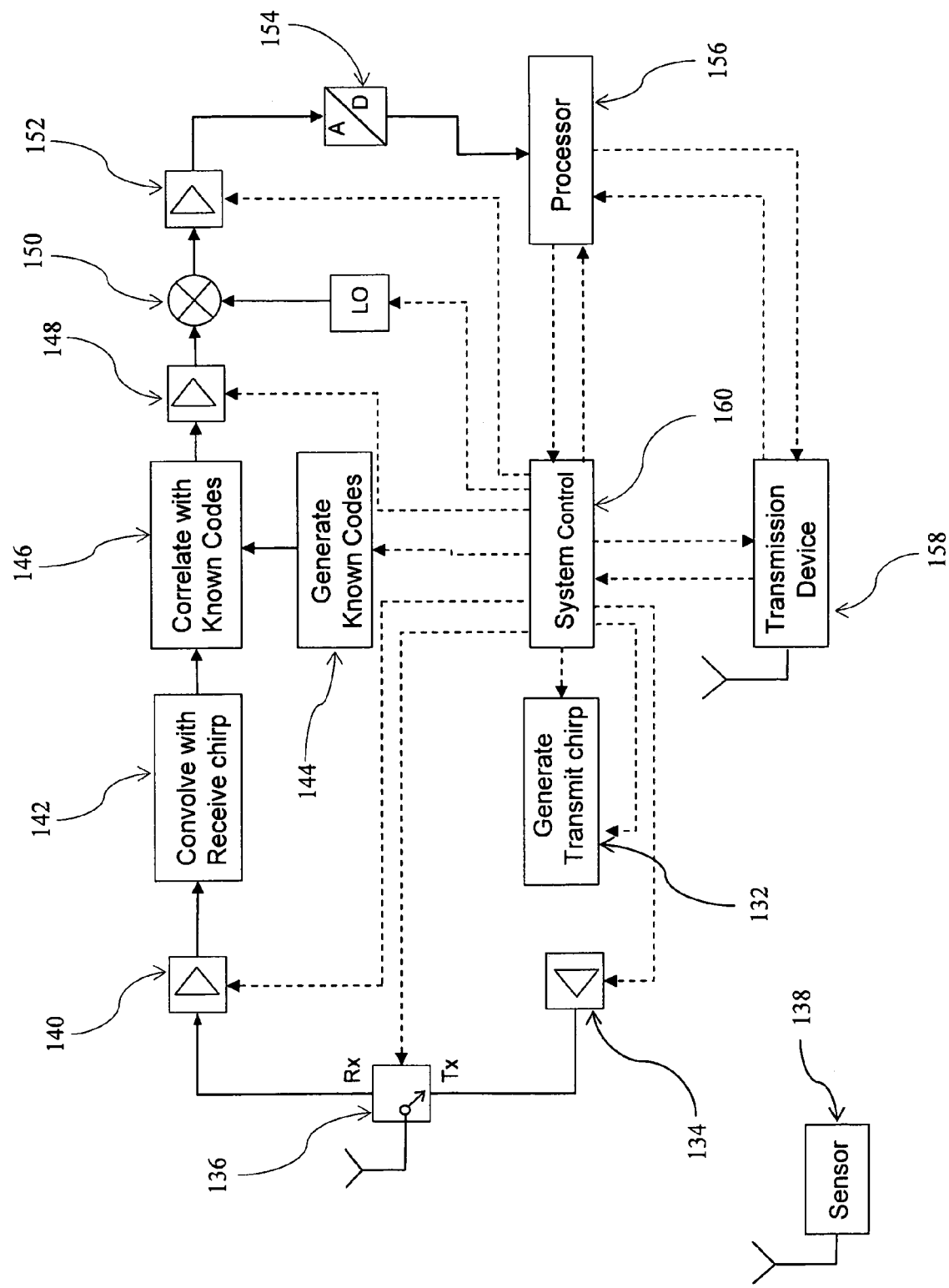
FIG. 13 is a block diagram of a transceiver system to be used with an orthogonal frequency coded sensor.

FIG. 13 shows the basic block diagram for a transceiver system to be used with OFC SAW sensors. Due to the nature of these sensors, this system has some unique attributes. In order to efficiently transmit power into the sensors, the interrogation signal generated by the transmitter is a spread spectrum signal matched to the spectrum of the sensor devices. This is shown in FIG. 13 by generating an interrogation signal using a transmit chirp device 132. The transmitted chirp signal is amplified by an amplifier 134 and transmitted by a transceiver 136. The chirp signal convolves with the OFC sensor response in the sensor 138, and the signal sent back to the transceiver 136 is a noise-like spread-spectrum signal. This received signal is amplified by an amplifier 140, convolved with a chirp that is the opposite of the transmit chirp in a convolution device 142 and correlated with known sensor codes from a known code generator 144 in a correlator 146. The correlator determines which sensor is responding or separates the overlapping responses of multiple sensors and to obtain compressed pulses for detection. The correlated signal is amplified in an amplifier 148 and mixed down to lower frequency (IF or baseband) in multiplier 150, amplified again by an amplifier 152, and then digitized in an analog to digital converter 154. The digital data is then processed in a processor 156 to detect the compressed pulses, to integrate each sensor response over multiple interrogations, and to calculate the hydrogen concentration at each sensor. This information is then communicated to the end user through a variety of means, with the option of wireless data transmission device 158 shown schematically in FIG. 11. A controller 160 controls the operation of the system.

Alternate transceiver systems, such as those using FMCW signal processing techniques, may be useful for measurement of SAW hydrogen sensors, and may provide advantages in terms of increased measurement resolution.

Other embodiments that utilize SAM siloxane films and palladium nanocluster films on SAW devices are within the scope of this invention, and can use either the resonance frequency of a SAW resonator (measured directly or derived using the Fourier Transform of the amplitude of the sensor impulse response), or the time delay of a SAW delay line (measured directly in an oscillator loop or transformed into a difference frequency as in an FMCW system) as the parameter measured to determine vapor concentration. In each of these embodiments, the interrogation system will have an architecture that is designed to operate with the selected SAW sensor(s). Interrogation systems for SAW sensors include pulsed radar architectures, Fourier transform measurement systems, and delay line and resonator-based oscillator systems. In general, all of these system architectures have the common elements of: RF signal generation, amplification, and transmission through an antenna to the sensor(s); RF signal reception through an antenna of the sensor response; amplification, signal processing, down-mixing, and digitizing of the sensor signal response; and digital data analysis to determine sensor response. Since SAW devices are linear, coherent systems can be used. Quadrature demodulation can be implemented in the receiver unit before sampling and digitizing. Reading the SAW sensor takes only a few microseconds, which allows for time integration of the sensor response over a short time period to include many RF responses. This enhances the signal-to-noise ratio (SNR), and each 12 dB increase in SNR doubles the device read-out distance.

The preferred embodiment of the interrogation system will include time integration of the sensor response(s). It will be apparent to those of ordinary skill in the art that the invention can be implemented as a single or multiple sensor system, with wired or wireless communication between the transceiver and the sensor(s). Multiple transceivers and/or signal repeaters may be utilized for large multi-sensor systems. Practical systems utilizing the invention may include a computer, microprocessor, or other calculating devices, and the necessary software for calculating hydrogen concentration based on measured sensor response(s). Such systems may include the ability to uniquely identify individual sensors and the data therefrom. Additional aspects of a practical system utilizing the invention include the ability to store data and calculation results, and devices for transmitting the data and/or results to entities interested in the results. Such transmission of information may include but is not limited to communicating to external computers, web sites, cell phones, and other devices.

While the preferred forms and embodiments of the invention have been illustrated and described, it will be apparent to those of ordinary skill in the art that various changes and modification may be made without deviating from the inventive concepts set forth above.

What is claimed is:

1. A hydrogen sensor, comprising
   (a) a piezoelectric substrate;
   (b) a self assembled monolayer arranged on at least a portion of said piezoelectric substrate to create a hydrophobic surface, said hydrophobic surface providing an interface to allow free movement of metal nanoclusters thereon;
   (c) a palladium nanocluster thin film deposited on at least a portion of said monolayer, said palladium nanocluster thin film having a structure such as to respond to hydrogen exposure by changing conductivity;
   (d) a first surface acoustic wave element comprising a transducer formed on a region of said piezoelectric substrate for transducing a signal; and
   (e) at least one second surface acoustic wave element formed on said piezoelectric substrate and spaced from said first surface acoustic wave element, said second surface acoustic wave element receiving said signal from said first surface acoustic wave element and generating a response signal, said response signal being modified by said palladium nanocluster film due to said change in conductivity of said palladium nanocluster film upon exposure to hydrogen.

2. A hydrogen sensor as defined in claim 1, wherein said monolayer and palladium nanocluster film is arranged between said first and second surface acoustic wave elements.

3. A hydrogen sensor as defined in claim 1, wherein said at least one second surface acoustic wave element comprises a transducer.

4. A hydrogen sensor as defined in claim 1, wherein said at least one second surface acoustic wave element comprises a reflector.

5. A hydrogen sensor as defined in claim 1, wherein said at least one second surface acoustic wave element comprises a pair of second surface acoustic wave elements connected with said piezoelectric substrate spaced from said first surface acoustic wave element.

6. A hydrogen sensor as defined in claim 1, wherein said palladium nanocluster thin film is formed in a pattern on said monolayer to define at least one variable resistance element electrically connected with at least one of said first and second surface acoustic wave elements.

7. A hydrogen sensor as defined in claim 1, wherein said first surface acoustic wave element comprises a coded element.

8. A hydrogen sensor as defined in claim 1, wherein said at least one second surface acoustic wave element comprises a coded element.

9. A hydrogen sensor as defined in claim 1, wherein said piezoelectric substrate is selected from a group of substrates having high electromechanical coupling including lithium niobate, lithium tantalate, langasite, langanite, langatate, and potassium niobate.

10. A hydrogen sensor as defined in claim 1, wherein said self assembled monolayer is composed of a siloxane containing compound.

11. A hydrogen sensor as defined in claim 1, wherein said palladium nanocluster thin film is composed of a palladium alloy.

12. A hydrogen sensor as claimed in claim 1, wherein said self assembled monolayer is approximately one molecule thick.

13. A hydrogen sensor as claimed in claim 1, wherein said palladium nanocluster thin film has a structure as a result of being formed by evaporation.

14. A hydrogen sensor as claimed in claim 1, wherein said palladium nanocluster thin film has a thickness of less than 5 nm.

15. A hydrogen sensor as claimed in claim 1, wherein said self assembled monolayer is substantially insensitive to hydrogen.

16. A system for measuring hydrogen concentration, comprising
   (a) at least one hydrogen sensor, including
      (1) a piezoelectric substrate;
      (2) a self assembled monolayer arranged on at least a portion of said piezoelectric substrate to create a hydrophobic surface;
      (3) a palladium nanocluster thin film deposited on at least a portion of said monolayer;
      (4) a first surface acoustic wave element comprising a transducer formed on a region of said piezoelectric substrate for transducing a signal; and
      (5) at least one second surface acoustic wave element formed on said piezoelectric substrate and spaced from said first surface acoustic wave element, said second transducing element receiving said signal from said first surface acoustic wave element and generating a response signal, said response signal being modified by said palladium nanocluster film due to a change in conductivity of said palladium nanocluster film upon exposure to hydrogen; and (b) an interrogator which transmits an interrogating signal to said hydrogen sensor and receives the response signal from said hydrogen sensor, said interrogator including (1) a voltage source for producing a source signal;

(2) an antenna for transmitting an interrogating signal from said source signal to said hydrogen sensor and for receiving the response signal therefrom; and (3) a signal processor for converting the response signal into a metric corresponding to the hydrogen concentration.

17. A system for measuring hydroen concentration, comprising:

(a) at least one hydrogen sensor, including (1) a piezoelectric substrate;

(2) a self assembled monolayer arranged on at least a portion of said piezoelectric substrate to create a hydrophobic surface;

(3) a palladium nanocluster thin film deposited on at least a portion of said monolayer;

(4) a first surface acoustic wave element comprising a transducer formed on a region of said piezoelectric substrate for transducing a signal; and (5) at least one second surface acoustic wave element formed on said piezoelectric substrate and spaced from said first surface acoustic wave element said second transducing element receiving said signal from said first surface acoustic wave element and generating a response signal, said response signal being modified by said palladium nanocluster film due to a change in conductivity of said palladium nanocluster film upon exposure to hydrogen; and (b) an interrogator which transmits an interrogating signal to said hydrogen sensor and receives the response signal from said hydrogen sensor said interrogator including (1) a voltage source for producing a source signal;

(2) an antenna for transmitting an interrogating signal from said source signal to said hydrogen sensor and for receiving the response signal therefrom;

(3) a signal processor for converting the response signal into a metric corresponding to the hydrogen concentration, (4) first and second delay devices connected with said voltage source for receiving the source signal and providing first and second reference signals, respectively;

(5) first and second multipliers connected with said first and second delay devices, respectively, and with said antenna for receiving the first and second reference signals and the response signal and for producing first and second product signals; and (6) first and second integrators connected with said first and second multipliers, respectively, for receiving the first and second product signals and providing signals indicative of at least one of hydrogen concentration and temperature at said sensor.

18. A system as defined in claim 17, wherein said voltage source comprises a pseudo noise signal generator and wherein said interrogator further includes a clock control unit connected between outputs of said integrators and said source signal to modulate the periodicity of said voltage source in order to generate a matching signal delay between the response signal and the reference signals.

* * * * *